(12) United States Patent
Benedikt et al.

(10) Patent No.: US 7,246,905 B2
(45) Date of Patent: *Jul. 24, 2007

(54) METHOD AND AN APPARATUS FOR THE SIMULTANEOUS DETERMINATION OF SURFACE TOPOMETRY AND BIOMETRY OF THE EYE

(76) Inventors: Jean Benedikt, Auf der Scheibe 30, D-88138, Sigmarszell (DE); Thomas K. Bende, Jahnstrasse 16, D-72116, Mossingen (DE); Adolf F. Fercher, Hassreitersteig3/11, A-1230, Wien (AT)

( * ) Notice: Subject to any disclaimer, the term of this patent is extended or adjusted under 35 U.S.C. 154(b) by 730 days.

This patent is subject to a terminal disclaimer.

(21) Appl. No.: 10/622,202

(22) Filed: Jul. 18, 2003

(65) Prior Publication Data

US 2004/0066489 A1    Apr. 8, 2004

Related U.S. Application Data

(63) Continuation-in-part of application No. 09/831,793, filed as application No. PCT/EP99/08782 on Nov. 15, 1999, now Pat. No. 6,601,956.

(30) Foreign Application Priority Data

Nov. 13, 1998  (DE) ................................. 198 52 331
Jun. 9, 1999   (DE) ................................. 199 26 274

(51) Int. Cl.
    *A61B 3/10*    (2006.01)

(52) U.S. Cl. ........................ 351/212; 351/210; 351/221
(58) Field of Classification Search ................ 351/205, 351/206, 209–216, 221, 246; 356/450
See application file for complete search history.

(56) References Cited

U.S. PATENT DOCUMENTS

| 5,491,524 | A  | 2/1996  | Hellmuth et al. |
| 5,493,109 | A  | 2/1996  | Wei et al. |
| 5,526,073 | A  | 6/1996  | Mattioli |
| 5,640,962 | A  | 6/1997  | Jean et al. |
| 5,684,562 | A  | 11/1997 | Fujieda |
| 6,070,981 | A  | 6/2000  | Mihashi et al. |
| 6,601,956 | B1 | 8/2003  | Jean et al. |

FOREIGN PATENT DOCUMENTS

| DE | 4322620 A1  | 7/1993 |
| DE | 4325494 A1  | 7/1993 |
| DE | 19713623 A1 | 4/1997 |
| EP | 0697611 A2  | 2/1996 |
| EP | 0705562 A1  | 4/1996 |
| WO | WO97/42891  | 11/1997 |

*Primary Examiner*—Huy Mai
(74) *Attorney, Agent, or Firm*—Steven J. Hultquist; Intellectual Property Technology Law

(57) ABSTRACT

An apparatus (10, 10') for detecting the surface topography of a cornea (24) of an eye (22) by dynamic or static projection of a pattern onto the surface of the cornea and detection of the pattern reflected by the cornea, providing preferably simultaneous detection of at least one optical property of a layer disposed beneath the cornea.

40 Claims, 6 Drawing Sheets

METHOD AND AN APPARATUS FOR THE SIMULTANEOUS DETERMINATION OF SURFACE TOPOMETRY AND BIOMETRY OF THE EYE

CROSS-REFERENCE TO RELATED APPLICATION

This is a continuation-in-part of U.S. patent app. Ser. No. 09/831,793, which was filed on Jul. 30, 2001 now U.S. Pat. No. 6,601,956 as a §371 application of International Patent Application No. PCT/EP99/08782 filed Nov. 15, 1999, which in turn claims priority to German Patent Applications No. 198 52 331.9 filed Nov. 13, 1998 and No. 199 26 274.8 filed Jun. 9, 1998.

FIELD OF THE INVENTION

The present invention relates to a method and an apparatus for detecting the surface topometry of the cornea of the eye with means for a dynamic or static projection of a pattern onto the surface of the cornea and means for detecting the pattern reflected or mirrored by the cornea. The term "layer" shall be understood hereinafter within the terms of tomography and is not limited to thin border layers between zones of different refractive indexes.

BACKGROUND OF THE INVENTION

A wide variety of methods and apparatuses for detecting the surface topography of the cornea are known in which patterns are projected statically (e.g. DE 43 25 494 A1) or dynamically (e.g. DE 43 22 620 A1) onto the cornea and the pattern reflected or mirrored from the cornea is detected. Such methods are usually called video-keratometry, or ring projection according to Placido, and have proven their worth in general practice. They allow a point-by-point measurement of the corneal surface (mostly with more than eight thousand measuring points) within a few milliseconds.

The topography of the surface of the cornea is deduced from the position of the projection points and the relative relationship of these points that usually form a ring pattern. The reflected pattern is usually recorded by a charge-coupled device (CCD) array, with the CCD array (e.g., the CCD array of a video camera) usually being disposed coaxially and concentrically at the end of a so-called Placido's cone. This set-up leads to the consequence, however, that a central corneal region which has a diameter of approx. 0.5 mm cannot be detected during the measurement, although it is the central optical zone of the cornea that is particularly relevant to the determination of the refractive power of the eye and typically forms the pass-through point of the visual axis. The so-called Stiles-Crawford effect leads to the consequence that the central corneal zone which is free from any patterns during the projection of Placido's patterns plays a special role with respect to the peripheral corneal regions in the eye's projection system.

Moreover, video-keratometry, which occasionally is also designated as video-topography, is unable to supply any information on the back surface of the cornea and the lower sections of the refractive system of the eye, in particular the front side and back side of the lens. The geometry of the boundary surface, the depth of the anterior chamber of the eye, the boundary surface properties and the topography of the lens, the distribution of density and the scattering body arrangements in the lens and the depth of the posterior chamber of the eye (as defined by the distance between lens and retina) are the prerequisites for increasing the precision of refractive measures on the cornea and for implantation-surgical interventions on the lens for the computer-aided detection and analysis of the refractive system of the optical properties of the entire eye in a patient.

Keeping this in mind, one object of the present invention is to provide a method and an apparatus that allow detecting in a simple and rapid manner both the entire substantial surface topography of the cornea and also at least one optical property of the layers of the eye disposed under the cornea.

SUMMARY OF THE INVENTION

This object is achieved by an apparatus of the kind mentioned hereinafter, in which means are provided for detecting at least one optical property of a layer disposed beneath the cornea of the eye. This object is also achieved by a method of the kind mentioned hereinafter, in which at least one optical property of a layer of the eye disposed beneath the cornea is detected parallel to the detecting process of the surface tomography of the cornea.

Such a set-up and such a method enable the required measurements to be performed in one process. This is substantially more pleasant for the person undergoing such a measurement. Moreover, this set-up also ensures that a detection of the optical properties of layers beneath the cornea occurs with a required local calibration, because such a local calibration is enabled by the detection of the surface topography of the cornea. It is thus no longer necessary that the person rigidly stares into the focusing light during the measurement of the optical properties of layers disposed beneath the cornea, which is physiological not possible. Rather, smaller deviations can be measured accordingly by the detected surface topography. Thus, the apparatus and the method of the present invention allow for the first time determination of the optical properties of the entire eye with adequately high local precision.

For example, the apparatus in accordance with one embodiment of the present invention may comprise at least one laser light source for generating laser beams, a detector for detecting the laser beams as generated by the laser light source, means for splitting the laser beams and deflecting at least a portion of the laser beams into the eye, preferably through the central corneal area (e.g., the central portion of the cornea surface that is equal to or less than ½ of the area of the total cornea surface), and then deflecting such portion of the laser beams as reflected by the eye onto the detector.

Such an apparatus allows comparing the surface topography and the overall refraction of the eye for determination of the influence and the data of the optical media disposed deeper in the eye. In addition, scattering image analyses can be obtained from the relevant components of the eye (such as cornea, lens, and retina). Particularly the topographically non-detectable central portion of the cornea surface can be detected topometrically and topographically with such apparatus.

Accordingly, laser beams can be produced in a method in accordance with the present invention by means of at least one laser light source and can be split and deflected in such a way that at least a portion of the laser beams is guided into the eye, and the laser beams that is reflected by the eye is subsequently guided to the detector and detected thereby.

Depending on the respective problem to be solved, the method can be performed in such a way that the profile of the wave front of laser beams that are directed at the eye are compared with the profile of the wave front of laser beams that are reflected by the eye. As an alternative or additional embodiment, the method can also be performed in such a way that the running periods of laser beams emitted into the eye are determined.

The measurements will be particularly precise and easy to perform when a Placido Topometer is used for projecting the pattern onto the surface of the cornea. In this process, the laser beam can be guided on their path towards the eye and back through the beam of the Placido Topometer for detecting the optical properties of layers disposed beneath the cornea. For this purpose suitable deflection means such as tilted mirrors or deviating prisms are used.

For determining the optical properties of layers disposed beneath the cornea it is possible to introduce a known beam profile or a known wave front of a laser source in the zone of the pupillary opening and to direct the same onto the cornea and the lower sections of the eye. By determining the profile form of a wave front that is reflected by the eye and by comparing such profile with the wave front that is sent into the eye, it is possible to detect the optical properties. A Hartmann-Shack detector is particularly suitable for this purpose. Such an arrangement will yield a particularly precise picture of the optical properties of the layers of the eye that are disposed beneath the cornea.

Alternatively or cumulatively, it is also possible to provide optical coherence tomography (OCT) in order to determine the optical properties of the layers disposed beneath the cornea. Such a coherence tomography has proven its worth and reliably supplies tomographs from the entire eye and also contains information on the layer thickness of the individual portions of the eye that are relevant for the refraction (biometry). In particular, the method and apparatus of the present invention can be used for a substantial improvement of optical coherence tomography because movement artifacts can be respectively corrected by the continuous simultaneous detection of the surface topography of the cornea. Mathematical calculations based on these surface topographies can be used to compensate for corneal movements during data acquisition, and can thus also be used to compensate the movement errors for the OCT measurement.

The corneal topography in the central corneal area (e.g., the central portion of the cornea surface that is equal to or less than ½ of the area of the total cornea surface) can also be determined in particular in such a way that in the central Placido-ring-free area of the cornea, a short-coherent measurement system, preferably a laser measurement system, is mirrored in and is aimed at the cornea and the lower sections of the eye coaxially to an optical axis extending through the pupil and the retina. In addition, the OCT offers the advantage of measuring the morphology and other optical features of the different layers inside the eye. For example, these data can be used to measure and analyze the corneal wound healing process in the stromal tissue after refractive surgery.

As the time needed to capture the OCT information is substantially longer than the topography acquisition time, several—instead of only one—topographies should be made during the OCT—acquisition, in order to detect and compensate movement artifacts caused by accidental eye movements.

The yet unsolved problem of the alignment of the measuring device with the cornea can be solved as follows: OCT as well as the wave front sensing device can be correlated to the topographer's reference point (e.g., the patients line of sight). This is achieved by using the same fixation light for the topography and the wave front sensing or OCT, enabling calculation in x/y coordinates the starting point of the data analysis.

OCT also provides morphological information of the relevant optical components of the eye (cornea, lens, vitreous) by acquiring layer-specific information, obtained by appropriate adjustment of the z-axis. In this manner, morphological, optical, densitometric data from inside the cornea and the lens can be obtained. As a diagnostic and topometric tool for refractive surgery, only the OCT can provide such data, relevant for diagnosis and therapy. The said morphological information can also be obtained by wavelength selection based on OCT alone or in combination with z-axis variation based data acquisition.

OCT measurements of more than one point (centrally and paracentrally) allow the measurement of the lens in situ. Such measurements can be achieved by splitting the OCT (either statically using prisms, or dynamically using a scanning device) and subsequently assessing the differences between each beam's run-time. Beam splitting in one of the described manners allows triangulation measurements of the lens position, which is essential morphometric information.

Apart a static projection of the Placido ring pattern onto the cornea (tear film), the corneal surface topography as well as the information of the OCT scan can be obtained, using a dynamic projection of one or more light sources. In this manner, the Purcyne images (1=surface cornea, 2=retrocorneal surface, 3=anterior lens surface, 4=posterior lens surface, 5=retina) can be used to measure the optical relevant surfaces.

BRIEF DESCRIPTION OF THE DRAWINGS

Further details and advantages of the present invention are provided by the following description in conjunction with the drawings of preferred embodiments of the present invention, which are selected merely as examples and are not to be understood in any way as limiting, wherein.

DETAILED DESCRIPTION OF THE INVENTION, AND PREFERRED EMBODIMENTS THEREOF

Figure 1:
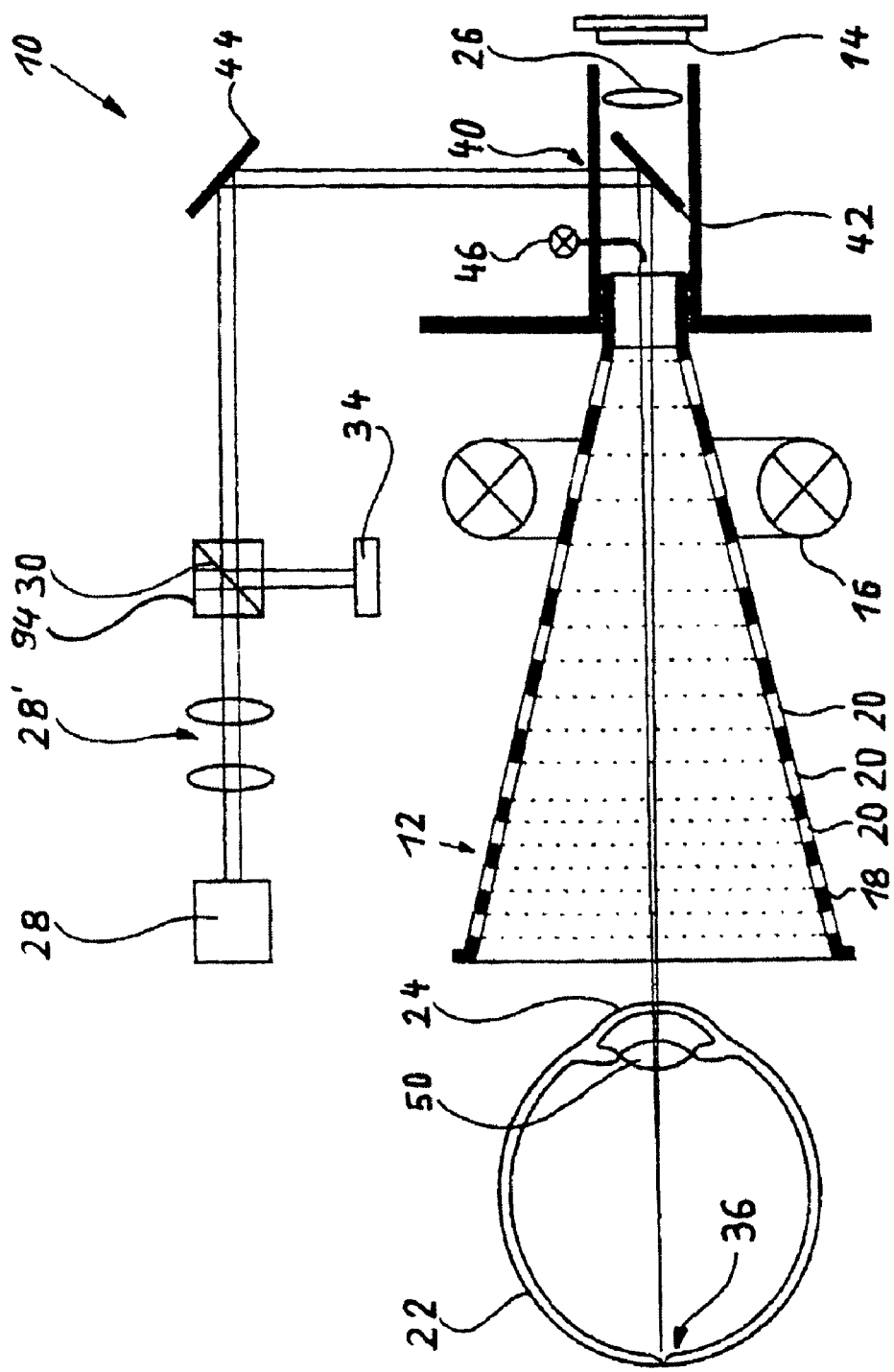
FIG. 1 shows the principal arrangement of an apparatus with a Placido Topometer and a wave front analyzer.
Figure 3:
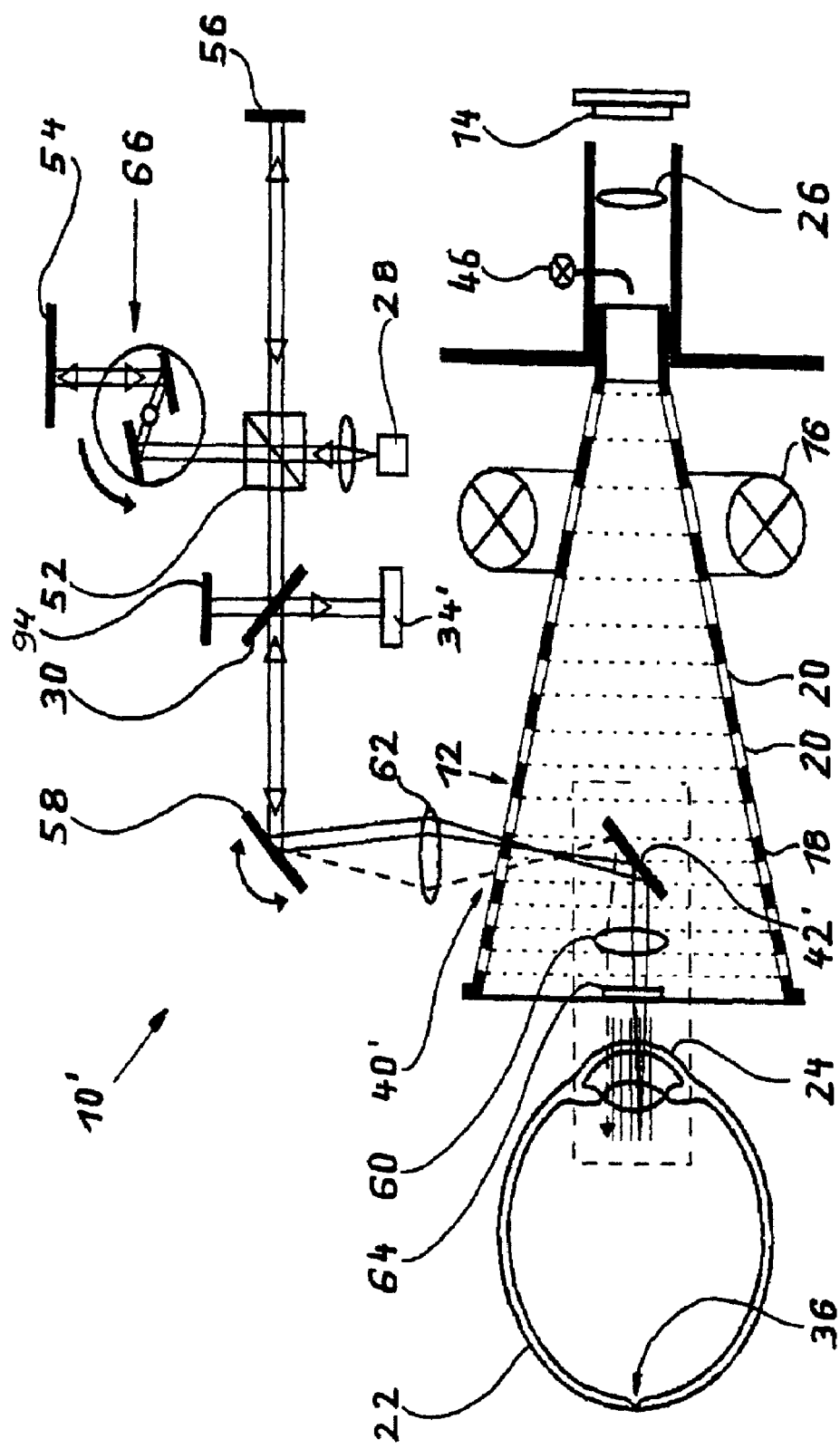
FIG. 3 schematically shows the arrangement of an apparatus with a Placido Topometer and optical coherence tomography (OCT), with the optical coherence tomography being set up for acquiring tomographs from the anterior section of the eye.
Figure 4:
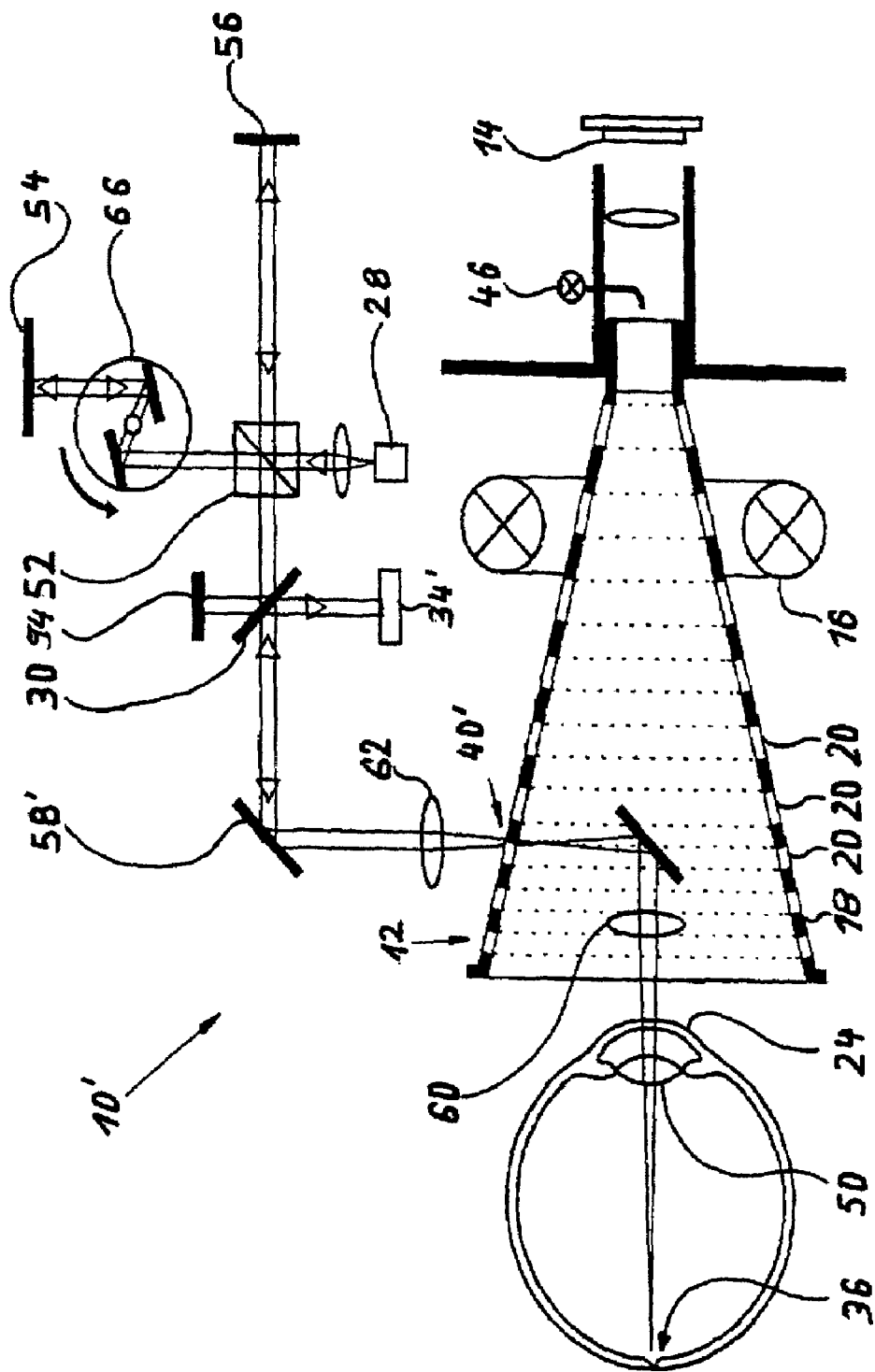
FIG. 4 shows the apparatus pursuant to FIG. 3, but with the coherence tomography being set up to perform scans in the middle and posterior section of the eye.

The apparatus, which is shown in FIGS. 1, 3 and 4 and is shown in its entirety with reference numerals 10 and 10', principally consists of two components, namely (1) a Placido Topometer with a Placido cone 12 with a random aperture angle, a CCD array 14 and an annular lamp 16 for illuminating the outside wall of the cone 18, and (2) a wave front analyzer, as shown in FIG. 1, or an optical coherence tomography, as shown in FIGS. 3 and 4.

A number of annularly extending apertures 20 are provided on the outside wall 18 of the Placido cone 12. Note that only a limited number of apertures are shown herein for illustration purposes. Light produced by the annular lamp 16 can pass through such apertures, so as to project a known pattern on an eye 22, or more specifically a cornea 24, to be examined. The annularly extending apertures 20 can concern slots in the simplest of cases, so that the projected rings are monochromatic. It is also possible to introduce various nets or grids into the apertures so that the projected rings are pattern-coded and a simpler allocation of the rings to their geometric origin is enabled. It is also possible to introduce different color filters into the individual apertures in order to thus encode the projected rings in color.

During the operation of the apparatus the luminous cone is reflected on a reflecting surface such as the surface of the cornea 24. The reflected image is reproduced via a lens 26 on the CCD array 14 of a video camera. The image of the surface with the reflected image of the cone rings is then supplied to an evaluator unit, e.g. a PC or a workstation, for further processing.

The Placido Topometer, which in the illustrated examples is a Placido ring topometer, allows measurement the surface of the cornea 24 within a few milliseconds by recording usually more than 8,000 measuring points. This has the disadvantage, however, that it does not supply any information from deeper sections of the eye. This information, however, can be supplied by the wave front analysis (as shown in FIGS. 1 and 2) or the coherence tomography (as shown in FIGS. 3 and 4), for the purpose of which the Placido Topometer is provided in accordance with the invention with a beam profile or wave front analyzer (as shown in FIGS. 1 and 2) or an optical coherence tomography (as shown in FIGS. 3 and 4).

Figure 2:
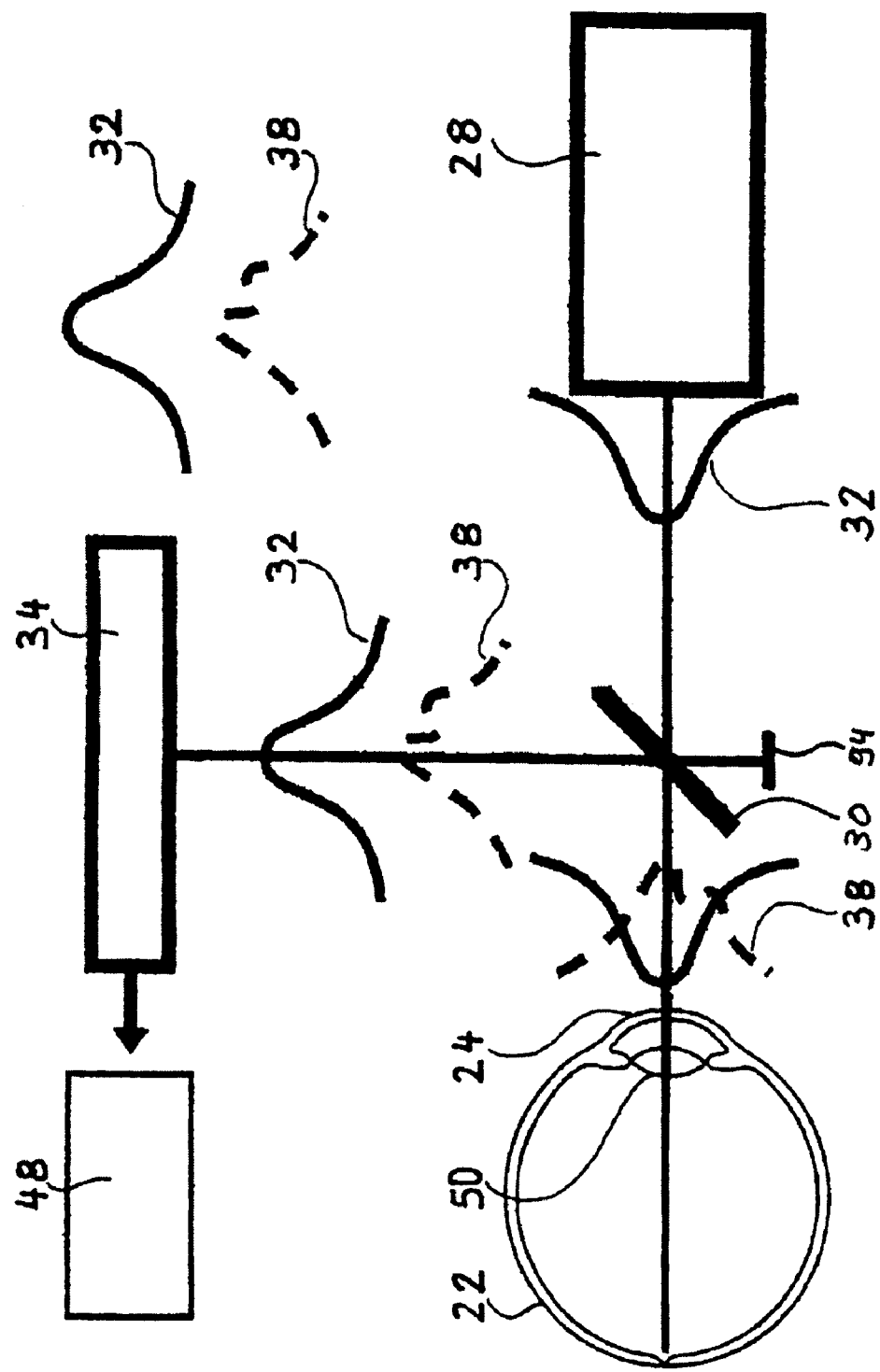
FIG. 2 shows the principal mode of operation of a wave front analyzer.

Referring to FIGS. 1 and 2, the beam profile or wave front analyzer consists of a laser source 28, which emits a beam profile in the known form, e.g., a Gaussian beam profile. This laser source 28 can emit an infrared or other light of known optical path length. The laser beam emitted by the laser source 28 is passed through a beam splitter 30 and split into two portions. The first portion of such laser beam is guided into a respective detector, e.g., a Hartmann-Shack sensor 34 by a mirror 94, so that the wave front 32 (as shown in FIG. 2) of such first portion of the laser beam can be read out by Hartmann-Shack sensor 34, and the profile of the wave front 32 can then be determined from the acquired data. The second portion of the laser beam, which is not mirrored out into the Hartmann-Shack sensor 34, is directed into the eye 22. The diameter of the laser beam as used herein depends on the pupil's diameter and can optionally be widened or reduced by a lens system (telescope 28') depending on the type of the laser source. The wave front 38 of the second portion of the laser beam as reflected on the retina 36 or the rear pole of the eye 22 is deflected on the partially transparent mirror (beam splitter 30) to the detector 34. The difference between the two wave fronts, namely the input wave front 32 and the reflected wave front 38, which were illustrated beneath one another in the right-hand upper portion of FIG. 2 so as to show their different forms, allows determination of the local differences in running time. This in turn allows determination of local differences in refraction. In conjunction with the surface topography, it is not only possible to describe the surface of the cornea with respect to form and curvature in local coding, but also to determine the influence of the deep-lying refractory media on the overall refractive power.

In order to combine the two measuring methods, an aperture 40 is introduced at any location in the beam path of the Placido Topometer (as shown in FIG. 1), through which the laser beam of the wave front analyzer can be guided. A small deviation mirror 42 is attached in the interior of the Placido cone 12, for redirecting the laser beam of the wave front analyzer either parallel or at a known angle to the axis of eye to the CCD array 14. Said deviation mirror 42 can be attached both centrally as well as outside of the center of the Placido cone 12. Instead of the deviation mirror, it is also possible to consider other beam-guiding objects (e.g., prisms). An optional deviation mirror 44 is provided in the embodiment as shown in FIG. 1, which can be omitted, depending on the arrangement of the laser light source 28.

Moreover, if the laser light emitted by the laser source 28 cannot be used as a so-called fixation light for the patient, the apparatus can be provided with an additional focusing light 46, which helps the patient being examined to keep the examined eye as steady as possible during the examination, by focusing on the focusing light 46.

Further, an evaluator 48 (as shown in FIG. 2) can be coupled with the detector 34 for data evaluation. A central evaluation and control unit, such as a PC, can be provided for evaluating the data received both from the CCD array 14 and from the detector 34, and for simultaneously controlling the apparatus according to the problem to be solved. The data thus obtained can be used, for example, for determining the overall optical behavior of the eye or important parts of the eye, such as the eye lens 50 for example. From the radius of curvature of the surface of the cornea and the information on the total refraction of the eye, it is possible for example to calculate with high precision the data of an artificial intraocular lens to be produced for a patient with a cataract.

In this process, the described measurements can be performed both within a recording sequence, and also sequentially. In addition, any desired combination of the individual measurements is possible within definable time intervals. Both measuring processes can be coordinated through respective automatic control processes, which control both the sequence of recordings as well as the selection of the required information, according to the problem to be solved. According to the problem to be solved, which is selected by the operator, for example, through a control menu, the measurements to be performed are chosen automatically and will then be executed in a sequence that is the most appropriate for the respective application. The results of the measurement can be output for example on a screen or a printer in the form of color-coded cards for the radii or elevation values of artificial lenses and/or as a computer file for further use such as during the automatic production of artificial lenses.

The combination of the methods leads to a qualitatively novel and previously unachievable quantitative description of the eye in respect of diagnostics and therapeutics. In combination with the method for determining the absolute coordinates in free space (cf. DE 195 163 09 AI), as developed by the applicant and a rapid calculation of ray tracing, it is possible for the first time to determine not only the optical boundary surfaces, but also the optical quality of the media in a metrologically objective manner. With the help of a Ray Tracing program, it is possible in vivo and in situ to quantify the overall refractive system, based upon the data acquired by the apparatus. Biometric data allow the individual analysis and prospective calculation of the visual acuity, contrast sensitivity as functional parameters. At the same time, the consequence of a planed surgical intervention (e.g., intrastromal ring, phacic IOL, PRK, LASIK) can be calculated and thus—in limits—predicted by an "expert" software program.

As a result of the combination of the methods, automated laser surgery is provided with a previously unattainable comprehensive topometrical/topographical illustration of the cornea, ranging from the outermost peripheral cornea up to the pass-through point of the visual axis through the cornea. This, on the other hand, leads to the opportunity to use the complete data record (possibly with its linkage to ray tracing programs) to introduce the individually optimal ablation pattern for the front surface of the cornea with photo-ablative lasers. The data thus gained can be used according to the method known under the name of "Assisted or Guided Topography", as a result of their completeness over the entire cross section of the cornea, to detach the ablation process from the surgeon's manual dexterity and to provide it as a data record for the automated ablation of tissue in the laser per se.

The topography of the cornea and the wave front analysis in the eye lead to new possibilities in the calculation of individually manufactured intraocular lenses. For the first time, they allow determining vision-optimized refractory conditions for the individual patient, both for medical care with contact lenses as well as with intraocular lenses. It is thus possible to seriously change the limits of previous medical care with contact lenses and with intraocular lens implants. Finally, this system is also based on an approach leading to cost reductions for the health system in general in which the additional corrective aids such as spectacles, which are still required in more than 70% of the cases, will become avoidable.

FIGS. 3 and 4 show an apparatus 10' substantially consisting of a Placido Topometer with a Placido cone 12, a cone lamp 16 and a CCD array 14, as well as an optical coherence tomography. An aperture 40' is provided on the Placido cone 12, through which the laser beam from the coherence tomography can be guided. A small deviating mirror 42' is attached in the interior of the Placido cone 12, which will redirect the laser beam from the coherence tomography either parallel or at a known angle to the axis of eye 22 to CCD array 14. Said deviation mirror 42' can be attached both centrally as well as outside of the center of the Placido cone 12. Instead of the deviation mirror, it is also possible to consider other beam-guiding objects (e.g., prisms).

The optical coherence tomography (OCT) per se consists substantially of (1) a laser light source 28, e.g., a so-called super-luminescent laser diode (SLD) may be used in the present invention as a laser light source, (2) a prism splitter 52 that splits the laser beam from the laser light source 28 onto two reference mirrors 54 and 56, and (3) a photodetector 34' that detects the running time, the phase shift, and the intensity behavior of the incident laser light. An additional deviation mirror 58 (as shown in FIG. 3) or 58' (as shown in FIG. 4) can be provided, which, as indicated by the arrowheads in FIG. 3, is swivelable about two axes, so that it can act as an "x/y scanner". Moreover, focusing lens systems (including lenses 60 and 62) for beam concentration are provided for the purpose of boundary surface detection and are positioned in such a way that the beam diameter is as small as possible at the pass-through point 40' of the laser beam on the Placido cone 12 and only a very small loss of information is incurred during the Placido measurement. A dual-beam reference mirror is further provided in the apparatus as shown in FIG. 3, for supplying a reference surface for the geometry of the cornea.

The focal point at which the laser beam is focused on its path into the eye after the last deviation mirror 42' defines the measuring point or the measuring plane of the coherence tomography. In order to detect the individual boundary surfaces on the eye for example (anterior and posterior surface of the cornea, anterior and posterior surface of the lens, fundus of the eye), the focal point must be moved along the optical axis through the eye. An example is given in the embodiment shown in FIGS. 3 and 4, by means of a rotating or oscillating double-mirror optical path length modulator 66, which is interposed in the beam path between prism splitter 52 and first reference mirror 54. As a result of the movement of the modulator, the focal point of the laser beam is guided from the anterior surface of the cornea to the fundus of the eye. A signal maximum occurs in detector 34' with a reference beam of reference mirror 94, at each optical boundary surface. As a result of the angle encoding of the optical path length modulator 66, it is possible to assign each reflection point to a linear measure. This means that one obtains distance information within the eye along the optical axis between each optical boundary surface. These data can be used for the overall biometry of the eye, for example.

If the deviation mirror 58, as shown in FIG. 3, is swivelably held about two axes, a surface scan can be performed in any desired plane. For this purpose, the optical path length modulator 66 is brought to a standstill, according to the desired target plane, and the incoming laser beam is directed by means of the deviation mirror 58 to different points within the plane. In this way, it is possible to measure with high precision the central portion of the cornea for example, which—as was already explained above—cannot be measured with the Placido Topometer as a result of its design limitations. Moreover, by the defined advance of the measuring plane (rotation of the optical path length modulator), it is possible to measure any desired number of closely following planes which will then in their entirety provide three-dimensional information on the measured volume and can supply additional information on structural changes in the optical system (scattering, absorption, reflection, etc.). Such a diagnostic statement was previously not possible.

The use of limited x/y positions (for example 3 or 4 Positions) provided by the mirror 58 allows the determination of the decentration or tilt of the lens if the surface topography is combined with the data of the OCT measurement.

As has already been mentioned in connection with FIGS. 1 and 2, the measurements with the Placido Topometer and the coherence tomography can be performed either simultaneously or sequentially. As has also already been explained above, the combination of Placido Topometry and coherence tomography leads to a qualitatively novel and previously unachievable quantitative description of the eye in respect of diagnostics and therapeutics. With the help of the ray tracing programs it is then possible in vivo and in situ to quantify the overall refractory system after the acquisition of the data with the apparatus in accordance with the invention, including clouding of media and scar formation in/the wound-healing progress. For example, apparatuses and methods in accordance with the present invention can be used to obtain layer-by-layer information on the scattering bodies, for which there is urgent need both with respect to forensic medicine as well as diagnostics. For example, after surgery on the cornea it is possible to determine an objective measure for the haze formation and wound healing without having to resort to the physically simplifying forward light scattering.

A further important application is the therapy and risk stratification of the cataract, which, with the increasing shift in the population's age structure, will later affect up to 100% of the population. The invention allows an objective determination of the corneal clouding. Our knowledge of the other properties of the entire optical refractory system, which also includes the anterior and posterior surface of the lens and the anterior and posterior surface of the cornea as well as the depth of the anterior chamber of the eye, will allow determining therefrom the visual acuity that can objectively be expected.

An objective grading of the clouding inside the anterior chamber and the lens can be produced from the correlation between the calculated visual acuity with the clinically observed one. Even gaining objective criteria for grading the stages of clouding phenomena in vivo and in vito alone will have far-reaching consequences for diagnosing and the therapy of highly endemic eye diseases.

The invention also enables a qualitatively decisive improvement in the field of biometry. Conventional biometries based on ultrasonic sound which are performed prior to cataract operations and the insertion of artificial lenses operate with simplifications which in the end do not allow for an individually optimal visual result. Since the posterior surface of the cornea was not quantitatively detectable to date, it was partly not possible to determine any curvatures of the lens and possible, even minimal, decenterings and dislocations, so that the lenses to be implanted were calculated imprecisely. The socioeconomic consequences of the procedure to date are considerable: up until now the theoretically possible maximum rate of visual acuity was not achieved in approx. 80% of all cases of lens implantations after cataract operations, so that cost-intensive corrections by means of spectacles were required. If the miscalculation between RA/LA is more than three dioptres, additional problems of anisometropy can occur. The present invention now allows for the first time by using surface topometry and coherence tomography and/or wave front analysis to determine a data record in a particularly simple way from which the optimal implant for every individual case can be calculated precisely.

Figure 5:
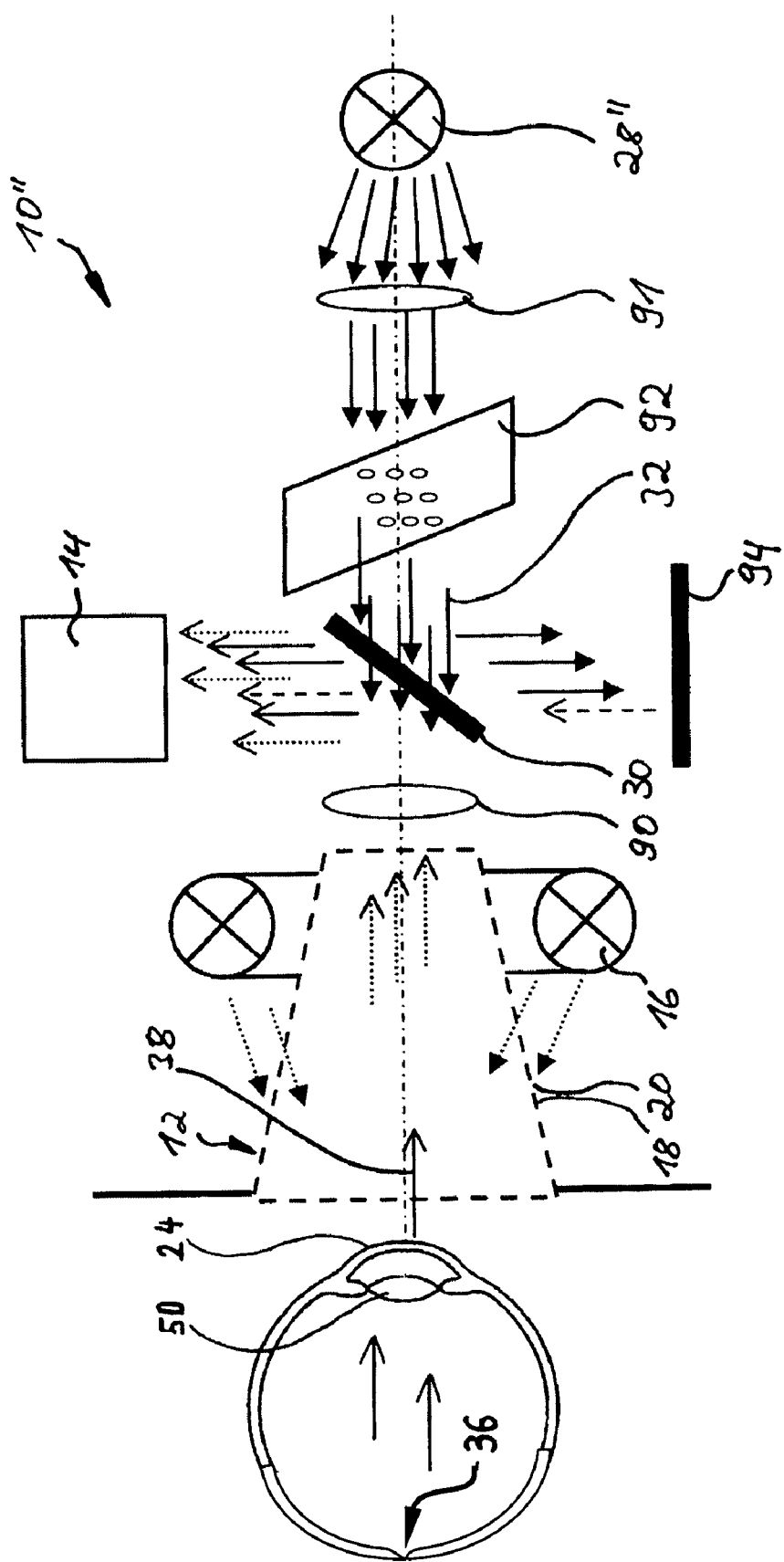
FIG. 5 schematically shows the arrangement of an apparatus with a Placido Topometer and a wave front analyzer comprising a conventional light source.
Figure 6:
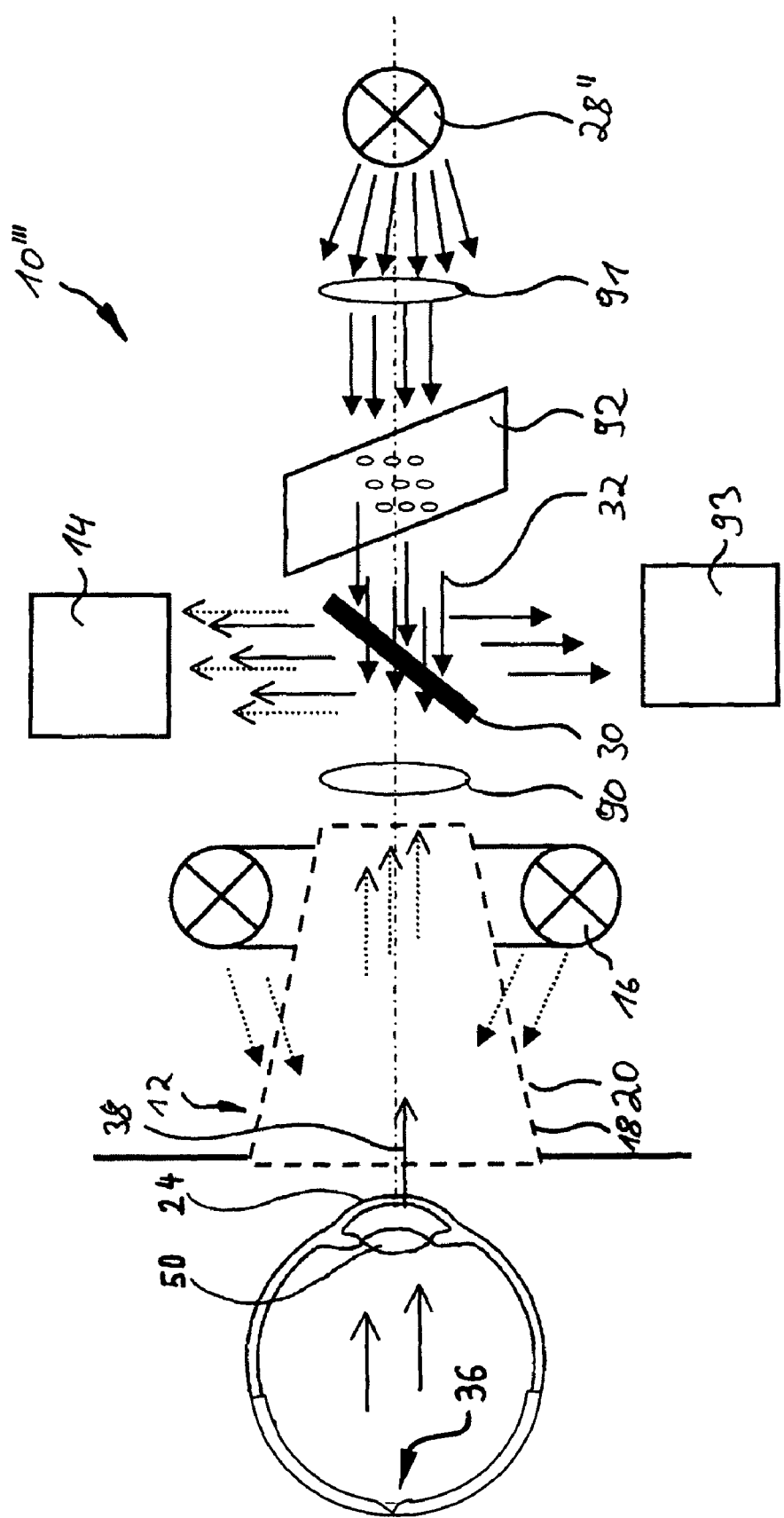
FIG. 6 schematically shows the arrangement of an apparatus with a Placido Topometer and a wave front analyzer comprising a conventional light source.

The apparatus shown in FIGS. 5 and 6 are shown in its entirety with reference numerals 10" and 10''', which principally consists of two components, namely (1) a Placido Topometer and (2) a wave front analyzer. Since a lot of the components of these apparatus are identical to the components of the apparatus shown in FIGS. 1 to 4, identical reference numerals are used for these components. The Placido Topometer comprises a cone 12 with a random aperture angle, a CCD array 14 and an annular lamp 16 for illuminating the outside wall 18 of the cone 12. A number of annularly extending apertures 20 are provided on the outside wall 18 of the Placido cone 12 (note that only a limited number of apertures are shown herein for illustrative purposes). Light produced by the cone lamp 16 can pass through such apertures 20 so as to project a known pattern on an eye 22, or more specifically on a cornea 24, to be examined. The annularly extending apertures 20 may comprise the features as they are already described with respect to the apparatus according to FIGS. 1, 3 and 4.

During the operation of the apparatus, the luminous cone is reflected on a reflecting surface such as the surface of the cornea 24. The reflected image is reproduced via a lens 90 and a beam splitter 30 on the CCD array 14 of a video camera. The image of the surface with the reflected image of the cone rings is then supplied to an evaluator unit, e.g. a PC or a workstation, for further processing.

The beam profile or wave front analyzer consists of a light source 28", which emits a laser beam with a known beam profile that is characterized by the properties of the light source 28" and the following optical beam forming members: (1) a lens 91 and (2) a diaphragm 92, which may be a kind that is different from that illustrated in FIGS. 5 and 6, depending on the system requirements. The wave front 32 of the laser beam emitted by the light source 28" is read out via the beam splitter 30 and mirror 94 by a respective detector, e.g., the CCD array 14, as shown in FIGS. 1 and 5, or a separate detector 93, as shown in FIG. 6. The profile of the wave front 32 is determined from the acquired data. The portion of the light that is not mirrored out is beamed into the eye 22. The wave front 38 as reflected on the retina 36 or the rear pole of the eye 22 is deflected on the partially transparent mirror (beam splitter 30) to the detector 14. The difference between the two wave fronts, namely input wave front 32 and the reflected wave front 38 allows determination of local differences in refraction. In conjunction with the surface topography, it is not only possible to describe the surface of the cornea with respect to form and curvature in local coding, but also possible to determine the influence of the deep-lying refractory media on the overall refractive power. According to the embodiments of FIGS. 5 and 6, the CCD array 14 is used for measuring the light from the Placido Topometer as well as the input/reflected wave fronts. In the embodiments according to FIGS. 1, 3 and 4 separate units are used for this purpose.

The measurement of the input wave front and the reflected wave front has the advantage that the wave fronts are simultaneously checked, so that minor defects of the input wave front will be detected and will not affect the result. Additionally, the wave front may be altered. With respect to the embodiments in FIGS. 5 and 6, the alteration of the wave front can be simply carried out by changing the light source 28" or the diaphragm 92.

Within the scope of the idea of the invention, it is possible to provide numerous modifications and further developments are possible which relate to the type and arrangement of the Placido Topometer for example. Thus it is possible for example not to produce the Placido pattern statically onto the cornea with the help of a Placido cone, but instead to produce the patterns dynamically by rotating light-emitting diodes (LEDs) for example. It is similarly possible that the laser light beamed in for the wave front analysis or the coherence tomography is projected statically or dynamically. The relevant aspect in the invention is in any case that topometer and wave front analyzer or coherence tomography are combined in one apparatus.

What is claimed is:

1. An apparatus for detecting the surface topography of a cornea of an eye, comprising:
   (a) a first light source for dynamically or statically projecting a light pattern onto a first surface area of the cornea;
   (b) a first detector for detecting the light pattern as reflected by the first surface area of said cornea;
   (c) a second light source for illuminating a component of said eye disposed beneath said cornea through a second surface area of the cornea with a second light; and
   (d) a second detector for detecting the second light as reflected back from said component of said eye beneath said cornea,
   wherein said second surface area comprises a central portion of the cornea surface, and
   wherein said first surface area surrounds said central portion of said cornea surface.

2. The apparatus according to claim 1, wherein said second light source comprises means for dynamically or statically projecting a light pattern onto said component of the eye beneath the surface of said cornea.

3. The apparatus according to claim 1, comprising at least one laser light source.

4. The apparatus according to claim 3, wherein said at least one detector determines the wave front profiles of the second light before its entry into the eye and as reflected by the eye.

5. The apparatus according to claim 1, wherein the first light source comprises a Placido Topometer, wherein the Placido Topometer is positioned in such a way that the second light from the second light source is guided through the beam path of the Placido Topometer to the eye, and that the second light as reflected back from said component of the said eye beneath the cornea is guided through the beam path of the Placido Topometer to the second detector.

6. The apparatus according to claim 1, wherein the second detector determines the wave front profile of said second light.

7. The apparatus according to claim 1, further comprising means for deflecting the second light and guiding said second light into the eye at different points of a plane.

8. The apparatus according to claim 7, wherein the means for deflecting and guiding the second light comprises at least one swivelable mirror.

9. An apparatus for detecting the surface topography of a cornea of an eye, comprising:
   (a) a first means for dynamically or statically projecting a light pattern onto a first surface area of the cornea, and
   (b) a second means for detecting the light pattern as reflected by said first surface area of the cornea;
   (c) a third means for determining at least one optical property of a component of the eye disposed beneath the cornea, based on reference measurement of an impinging light that is directed into the eye.

10. The apparatus according to claim 9, wherein the third means measures said impinging light before its entry into the eye, directs said impinging light to illuminate said component of the eye beneath the cornea through a second surface area of the cornea, and then measures the impinging light as reflected by said component of the eye beneath the cornea.

11. The apparatus according to claim 10, wherein the first means comprises a Placido Topometer, which is positioned in such a way that the impinging light is guided through the beam path of the Placido Topometer to the eye, and that the impinging light as reflected back from said component of the said eye beneath the cornea is guided through the beam path of the Placido Topometer to be detected.

12. The apparatus according to claim 10, wherein the third means determines the wave front profile of said impinging light.

13. The apparatus according to claim 10, wherein the third means further deflects the impinging light and guides said impinging light into the eye at different points of a plane.

14. The apparatus according to claim 13, wherein the means for deflecting and guiding the impinging light comprises at least one swivelable mirror.

15. The apparatus according to claim 9, wherein said third means comprising a beam splitter for splitting the impinging light into at least two portions, and wherein a first portion of the impinging light is used for reference measurement.

16. The apparatus according to claim 15, wherein said beam splitter comprises a prism splitter.

17. The apparatus according to claim 15, whereby said third means further comprises at least one reference mirror for guiding said first portion of the impinging light for measurement.

18. The apparatus according to claim 9, comprising at least one laser light source.

19. A method for detecting the surface topography of a cornea of the eye, comprising the steps of:
   (a) dynamically and statically projecting a light pattern onto a first surface area of the cornea;
   (b) detecting the light pattern as reflected by said first surface area of the cornea;
   (c) illuminating a component of said eye disposed beneath said cornea through a second surface area of the cornea with an impinging light; and
   (d) detecting the impinging light as reflected back from said component of the eye beneath the cornea,
   wherein the second surface area comprises a central portion of the cornea surface, and
   wherein the first surface area surrounds said central portion of the cornea surface.

20. The method according to claim 19, further comprising the step of dynamically or statically projecting a light pattern beneath the cornea surface.

21. The method according to claim 19, further comprising the steps of evaluating wave front of the reflected impinging light, and determining the overall distribution of refractive power of the eye with local encoding based on the evaluation.

22. The method according to claim 19, further comprising the steps of determining one or more properties of the eye based on the detected data, wherein said properties include: size of the cornea surface, size of posterior surface of the cornea, size of anterior surface of the lens, size of posterior surface of the lens, size of surface of the retina, radius of curvature, refractive power, and absolute height value of the cornea.

23. The method according to claim 19, wherein information on the optical boundary surfaces of the refractive apparatus of the eye is determined along an optical axis from the pupillary aperture up to the retina.

24. The method according to claim 19, wherein the impinging light is focused on a focal point in the eye, wherein said focal point is moved along the optical axis extending from the cornea to the retina, and wherein reflection maxima are determined along said optical axis.

25. The method according to claim 19, wherein the impinging light is focused on a focal point in the eye, wherein said focal point is moved in a plane perpendicular to the optical axis extending from the cornea to the retina, and wherein the reflection of the impinging light is measured at different points in this plane.

26. A method for detecting the surface topography of a cornea of an eye, comprising the steps of:
   (a) dynamically or statically projecting a light pattern onto a first surface area of the cornea;
   (b) detecting the pattern reflected by said first surface area of the cornea;
   (c) providing an impinging light;
   (d) measuring said impinging light before its entry into the eye;
   (e) directing said impinging light to illuminate said component of the eye beneath the cornea through a second surface area of the cornea;
   (f) measuring the impinging light as reflected by said component of the eye beneath the cornea; and (g) determining at least one optical property of said component beneath the cornea, based on measurements of the impinging light.

27. The method according to claim 26, wherein an impinging light of known beam profile and/or wave front is impinged into the zone of a pupillary aperture of the eye, and then and directed onto the cornea and the lower sections of the eye.

28. The method according to claim 26, comprising the steps of determining and comparing the wave front profile of said impinging light before its entry into the eye and the wave front profile of said impinging light as reflected by the eye.

29. The method according to claim 28, wherein the wave front profile of the impinging light before its entry into the eye is determined by splitting the impinging light into at least two portions, guiding a first portion of said impinging light directly or indirectly onto a detector, and guiding a second portion of said impinging light into the eye.

30. The method according to claim 28, wherein the overall distribution of refractive power of the eye is determined with local encoding by evaluating the wave front profile of the impinging light as reflected by the eye.

31. The method according to claim 26, comprising the step of determining one or more properties of the eye includeing: size of the cornea surface, size of posterior surface of the cornea, size of anterior surface of the lens, size of posterior surface of the lens, size of surface of the retina, radius of curvature, refractive power, and absolute height value of the cornea.

32. The method according to claim 26, wherein information on the optical boundary surfaces of the refractive apparatus of the eye is determined along an optical axis from the pupillary aperture up to the retina.

33. The method according to claim 26, wherein the impinging light is focused on a focal point in the eye, wherein said focal point is moved along the optical axis extending from the cornea to the retina, and wherein reflection maxima are determined along said optical axis.

34. The method according to claim 26, wherein the impinging light is focused on a focal point in the eye, wherein the focal point is moved in a plane perpendicular to the optical axis extending from the cornea to the retina, and wherein the reflection of the second light introduced into the eye is measured at different points in this plane.

35. An apparatus for detecting the surface topography of a cornea of an eye, comprising:
   (a) a first light source for dynamically or statically projecting a first light of a known pattern onto a first surface area of the cornea;
   (b) a second light source for illuminating a component of said eye disposed beneath said cornea through a second surface area of the cornea with a second light; and
   (c) at least one detector for detecting the first light and the second light as reflected back by the eye,
   wherein said second surface area comprises a central portion of the cornea surface, and
   wherein said first surface area surrounds said central portion of said cornea surface.

36. The apparatus according to claim 35, wherein said at least one detector detects the second light before its entry into the eye, and wherein at least one optical property of said component of the eye beneath the cornea is determined based on detection of the second light before its entry into the eye and as reflected by the eye.

37. The apparatus according to claim 36, wherein said at least one detector determines the wave front profiles of the second light before its entry into the eye and as reflected by the eye.

38. The apparatus according to claim 35, comprising a single detector for detecting the first light and the second light as reflected back by the eye.

39. The apparatus according to claim 35, comprising a first detector for detecting the first light as reflected, and a second detector for detecting the second light as reflected.

40. The apparatus according to claim 39, wherein said second detector detects the second light before its entry into the eye, and wherein at least one optical property of said component of the eye beneath the cornea is determined based on detection of the second light before its entry into the eye and as reflected by the eye.

* * * * *